United States Patent [19]
Cardin et al.

[11] Patent Number: 5,672,625
[45] Date of Patent: Sep. 30, 1997

[54] SULFONIC STILBENE DERIVATIVES IN THE TREATMENT OF VIRAL DISEASES

[75] Inventors: Alan D. Cardin, Cincinnati, Ohio; A. Stanley Tyms, London, England

[73] Assignee: Merrell Pharmaceuticals Inc., Cincinnati, Ohio

[21] Appl. No.: 463,582

[22] Filed: Jun. 5, 1995

Related U.S. Application Data

[62] Division of Ser. No. 248,851, May 25, 1994, Pat. No. 5,494,932, which is a continuation of Ser. No. 8,254, Jan. 25, 1993, abandoned, which is a continuation of Ser. No. 829,132, Jan. 31, 1992, abandoned.

[51] Int. Cl.$^6$ .................... A61K 31/165; A61K 31/26
[52] U.S. Cl. .................... 514/514; 514/516; 514/616
[58] Field of Search .................... 514/514, 516, 514/616

[56] References Cited

U.S. PATENT DOCUMENTS

| | | | |
|---|---|---|---|
| 4,328,244 | 5/1982 | Daniel et al. | 424/304 |
| 4,349,568 | 9/1982 | Markley et al. | 424/330 |
| 4,435,394 | 3/1984 | Ogata et al. | 424/248.5 |
| 5,124,149 | 6/1992 | Shapiro et al. | 424/93 |
| 5,276,182 | 1/1994 | Cardin et al. | 564/49 |

FOREIGN PATENT DOCUMENTS

| | | |
|---|---|---|
| 660945 | 11/1965 | Belgium. |
| 0221021 | 5/1987 | European Pat. Off.. |
| 0498095 | 5/1991 | European Pat. Off.. |
| 0467185 | 8/1991 | European Pat. Off.. |
| 2179347 | 3/1987 | United Kingdom. |
| 8800828 | 2/1988 | WIPO. |
| 9200749 | 1/1992 | WIPO. |
| 9314146 | 7/1993 | WIPO. |

OTHER PUBLICATIONS

Beigel et al., *Exp. Cell Res* 126, pp. 448–453 (1980).
Cabantchik et al., *J. Membrane Biol.* 10, pp. 311–330 (1972).
Rosoff et al., *J.Med. Chem.* vol. 263, No. 36, pp. 19535–19540 (1988).
Kawasaki et al., *J. Biochem* 106, pp. 401–405 (1989).
Huang et al., *Molecular Pharmacology*, 37, pp. 304–310 (1989).
Hofferek et al., Chemical Abstracts vol. 114: 180333q (1990).
Komp et al., Chemical Abstracts vol. 110: 33727k (1989).
Holt et al, Chemical Abstracts, vol. 81, No. 8, 26 Aug. 1974, Abstract No. 38919S.
Yamashita, *Chemical Abstracts, vol. 76, No. 12* 20 Mar. 1972, Abstract No. 60909g.
Yamashita, *Chemical Abstracts, vol. 74, No. 22* 31 May 1971 Abstract No. 113191j.
Mayrand et al, *Chemical Abstracts vol. 98, No. 17*, 25 Apr. 1983, Abstract No. 141183x.
Sugihara, *Chemical Abstracts, vol. 112, No. 3* 15 Jan. 1990, abstract No. 18775x.
Aleksandrov et al, *Chemical Abstracts, vol. 85 No. 5*, 2 Aug. 1976, abstract No. 32589v.
Zaki et al, *Chemical Abstracts vol. 84, No. 11*, 15 Mar. 1976, abstract No. 69813u.
Lorke, *Chemical Abstracts vol. 82, No. 15*, 14 Apr. 1975, Abstract No. 93787t.
Yamashita, *Chemical Abstracts vol. 78 No. 6* 12 Feb. 1973, Abstract No. 31400v.
*Classification and Nomenclature of Viruses*, Fifth Report of the International Commitee on Taxonomy of Viruses, pp. 357–359 (1991).
Brunken et al, *Chemical Abstracts, vol. 64, No. 3* 31 Jan. 1966.
Zheltov et al, *Chemical Abstracts vol. 73, No. 5*, 3 Aug. 1970 abstract No. 25375w.
Ohkubo et al, *Chemical Abstracts, vol. 78, No. 16* 23 Apr. 1973 abstract No. 98989n.
Lamparsky et al, *Chemical Abstracts vol. 53, No. 3* 10 Feb. 1959 abstract No. i.
Killman et al, *Chemical Abstracts vol. 77, No. 2* 10 Jul. 1972 abstract No. 7276t.

*Primary Examiner*—Phyllis G. Spivack
*Attorney, Agent, or Firm*—William R. Boudreaux

[57] ABSTRACT

Sulfonic acid stilbenes block the infection of cells by HSV and CMV and these compounds can be used to treat viral infection.

4 Claims, 2 Drawing Sheets

SULFONIC STILBENE DERIVATIVES IN THE TREATMENT OF VIRAL DISEASES

This is a division of application Ser. No. 08/248,851, filed May 25, 1994, now U.S. Pat. No. 5,494,932, which is a continuation of application Ser. No. 08/008,254, filed Jan. 25, 1993, now abandoned, which is a continuation of application Ser. No. 07/829,132, filed Jan. 31, 1992, now abandoned, which is herein incorporated by reference.

BACKGROUND OF THE INVENTION

A great deal of research is currently underway to develop treatments and cures for viral infections in humans and in animals. Notably the incidence of AIDS and ARC in humans is increasing at an alarming rate. The five year survival rate for those with AIDS is dispiriting and AIDS patients, whose immune systems have been seriously impaired by the infection, suffer from numerous opportunistic infections including Kaposi's sarcoma and Pneumocystis carninii pneumonia. No cure for AIDS is known and current treatments are largely without adequate proof of efficacy and have numerous untoward side effects. Fear of the disease has resulted in social ostracism of and discrimination against those having or suspected of having the disease.

Retroviruses are a class of ribonucleic acid (RNA) viruses that replicate by using reverse transcriptase to form a strand of complementary DNA (cDNA) from which a double stranded, proviral DNA is produced. This proviral DNA is then incorporated into the chromasomal DNA of the host cell making possible viral replication by transcription of this integrated DNA and translation of viral messenger RNA into proteins; assembly of new viral RNA into a protein core and release from the cell results in the formation of infectious virus progeny.

Many of the known retroviruses are oncogenic or tumor causing. Indeed the first two human retroviruses discovered, denoted human T-cell leukemia virus I and II or HTLV-I and II, were found to cause rare leukemias in humans after infection of T-lymphocytes. The third such human virus to be discovered, HTLV-III, now referred to as HIV, was found to cause cell death after infection of T-lymphocytes and has been identified as the causative agent of acquired immune deficiency syndrome (AIDS) and AIDS related complex (ARC).

The envelope protein of HIV is a 160 kDa glycoprotein. The protein is cleaved by a protease to give a 120 kDa external protein, gp 120, and a transmembrane glycoprotein, gp 41. The gp 120 protein contains the amino acid sequence that recognizes the receptor on CD4-positive human T-helper cells. Recently it was reported that the polysulfated polysaccharides dextran sulfate, carrageenans of sea algae, pentosan polysulfate, and heparin are highly effective inhibitors of HIV-1 replication invitro. M. Ito, et al., (1987) *Antiviral. Res.* 7, 361–367. Baba et al., *Antiviral Res.* 9, 335–343 (1988). O. Yoshida (1988) *Biochem. Pharmacol.* 37, 2887–2981. R. Ueno and S. Kuno, (1987) *Lancet* i, 1379. The presence of the sulfate groups on these molecules is required for the antiviral activity. The mechanism of this activity has been studied by Baba et al., (1988) *Proc. Natl. Acad. Sci. USA*, 85, 6132–6136.

Applicants have discovered that a class of sulfonated stilbenes that bear sulfonic acid groups are active against HIV. Herpes Simplex Viruses (HSV) I and II as well cytomegalovirus (CMV) have functionally related glycoprotein coatings and viral infectivity can also be diminished or eliminated by the use of the sulfonated stilbenes of this invention.

SUMMARY OF THE INVENTION

Compounds of formula 1 wherein $R_1$ and $R_2$ are each independently a $H_2N-$, $O_2N-$, $S=C=N-$, $N\equiv C-$, or $CH_3C(O)NH-$ group, B is a $-CH=CH-$ (cis or trans), $-C\equiv C-$, or $-CH_2-CH_2-$ group, and

$M_1$ and $M_2$ are each independently a hydrogen or a pharmaceutically acceptable cation are useful in the treatment of diseases caused by infections of eneloped viruses.

DETAILED DESCRIPTION OF THE INVENTION

The pharmaceutically acceptable cations are those cations that are not substantially toxic at the dosage administered to achieve the desired effect and do not independently possess significant pharmacological activity. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabiethylamine, N-(lower)alkylpiperidine, and any other suitable amine. Sodium salts are preferred.

The compounds of this invention are readily prepared by the ordinary artisan. The compounds are sulfonated derivatives of stilbene and can be prepared several ways by well known aromatic electrophilic substitution techniques such as are taught in R. T. Morrison and R. N. Boyd, *Organic Chemistry*, 5th ed., Allyn and Bacon, Inc., Boston, 1987, chap. 14. In general, the most efficient way to make the compounds of formula 1 is to sulfonate the corresponding nonsulfonated compound of formula 1a wherein B, $R_1$, and $R_2$ are as defined above for the compounds of formula 1 or are groups readily transformable into such substituents. Also, in general, when it is desired to prepare compounds of formula 1 or 1a wherein B is other than $-HC=CH-$, the corresponding compound wherein B is a $-HC=CH-$ is first prepared and subsequently the carbon-carbon bond is transformed by well known techniques to produce the desired moiety.

The compounds of formula 1a wherein B is a $-HC=CH-$ can be prepared, for example, by subjecting an optionally substituted benzaldehyde to a benzoin condensation as shown in Scheme A to form an initial keto-alcohol adduct of formula 2

SCHEME A wherein the B, $R_1$, and $R_2$ groups are as defined above for the compounds of formula 1 or are groups which can be subsequently converted to the groups defined above. For a good general review of the benzoin condensation reaction see Ide and Buck, Org. Reactions 4, 269–304 (1948). The formula 2 intermediate is then reduced to form a stilbene derivative, i.e. a compound of formula 1a wherein B is a —HC=CH— group. The reduction can be carried out in any conventional manner such as by use of a dissolving metal reduction technique using, for example, a zinc amalgam and a dilute acid such as acetic acid. The reduction usually results in a mixture of stilbenes of cis and trans geometric configuration relative to the carbon-carbon double bond, with the trans configuration preferred. One isomer can be converted to the other isomer in any manner generally used by those skilled in the art to convert geometric isomers relative to a carbon-carbon double bond. For example, a trans stilbene can be converted into a cis stilbene by the action of UV light.

Another approach to preparing the stilbenes of this invention is illustrated in scheme B. This reaction scheme involves the reaction of an aldehyde of formula 3 with a benzyl Grignard of formula 4 to form an alcohol of formula 5, which upon dehydration yields the desired stilbene. The substituents B, $R_1$, and $R_2$ of the formula 3, 4, and 5 compounds are as defined above for the compounds of formula 1 or are groups which can be subsequently converted to such substituents.

SCHEME B

Another approach to the preparation of the stilbenes of formula 1a is illustrated in scheme C involves the reaction of the aldehyde of formula 3 with an alpha-phenyl acetate of formula 6 to form an alcohol ester of formula 7 which upon dehydration gives the acrylate of formula 8 and which upon acid promoted decarboxylation gives the stilbene of formula 1a.

SCHEME C

Applicants prefer those compounds of formula 1 wherein B is a —$CH_2$—$CH_2$ group and more prefer those wherein B is a —CH=CH— group, especially those of the trans configuration. Applicants also prefer those compounds of formula 1 wherein $R_1$ and $R_2$ are each independently a S=C=N— or a $CH_3C(O)NH$— group. Applicants further prefer those compounds of formula 1 wherein $M_1$ and $M_2$ are each independently a hydrogen or a sodium cation. Applicants prefer those compounds wherein the $R_1$ and $R_2$ groups are in the para (or 4) position relative to the carbon to which the B group is attached and wherein the sulfonyl groups are in the γ ortho (or 2) position relative to the carbon atom to which the B group is attached. The preferred compounds of this invention are 4,4'-diisothiocyanatodihydrostilbene-2,2'-disulfonic acid ($H_2$DIDS), 4-acetamido-4'-isothiocyantostilbene-2,2'-disulfonic acid (SITS) and especially 4,4'-diisothiocyanatostilbene-2,2'-disulfonic acid (DIDS).

The sulfonated stilbenes can be used to prevent infection of cells with HIV and syncytium formation in cells with established HIV infections, or against other related viruses having gp120 surface protein as well the Herpes Simplex Viruses (HSV) I and II and the cytomegalovirus (CMV). The sulfonated stilbenes can be used to treat AIDS and ARC and other diseases caused by the retrovirus HIV or other related viruses having gp120 surface protein as well as diseases caused by the Herpes Simplex Viruses (HSV) I and II and cytomegalovirus (CMV).

When evaluated in the human T cell line JM acutely infected with the GB8 virus, DIDS, H$_2$DIDS and SITS (Table I) suppressed virus-induced multinucleated giant cell formation (syncytia). The antiviral activity of these compounds was confirmed by the dose-dependent inhibition of p24 viral core antigen (Table I) and by the absence of viral infectivity in the cell-free supernatants (data not shown). We also examined the antiviral properties of these compounds in a second host-cell/virus system, i.e., the highly CD4$^+$ C8166 cells infected with the Haitian strain of HIV-1, RF. As above, DIDS and H$_2$DIDS blocked HIV-1 infection; however, SITS at 100 µg/ml was inactive as determined by the syncytial and p24 antigen assays (Table I). DIDS and H$_2$DIDS also blocked the growth of RF in MT-4 cells at concentrations that were noncytotoxic as determined by the tetrazolium reduction assay method (Nakashima et al., 1989), whereas SITS only had weak antiviral activity (not shown). In all three host cell/virus systems, the antiviral potency was consistently DIDS>H$_2$DIDS>>SITS.

TABLE I

ANTIVIRAL ACTIVITY OF THE STILBENE DISULFONIC ACID ANALOGS DIDS, H$_2$DIDS AND SITS AGAINST INFECTION OF JM CELLS WITH HIV-1 STRAINS GB8 AND RF

| Compound | Concentration µM | Mean Syncytial[a] Counts | P24 Antigen[b] % Virus Control | |
|---|---|---|---|---|
| Virus Control | — | 101 | 100 | |
| DIDS | 200 | 0 | 0.02 | (4.8)[c] |
| | 100 | 0 | 0.56 | (33) |
| | 50 | 0 | 6.4 | (83) |
| | 25 | 31 | 100 | (100) |
| | 12 | 101 | — | — |
| | 6 | 114 | — | — |
| H$_2$DIDS | 200 | 0 | 0 | (2.5) |
| | 100 | 0 | 0.01 | (59) |
| | 50 | 7 | 43 | (>100) |
| | 25 | 71 | 100 | — |
| | 12 | 97 | 100 | — |
| | 6 | 107 | — | — |
| SITS | 200 | 0 | 1.6 | (>100) |
| | 100 | 15 | 85 | (>100) |
| | 50 | 63 | 100 | (>100) |
| | 25 | 63 | — | — |
| | 12 | 72 | — | — |
| | 6 | 93 | — | — |

[a]At day 4 p.i.
[b]Virus control = 7.35 × 10$^4$ pg/ml at day 6 p.i.
[c]Values in parenthesis are for the RF strain of HIV-1 in C8166 cells.

The stilbene disulfonic acids blocked HIV-1 replication when the compounds were added within 2 hours of virus adsorption, i.e., prior to virus penetration, and the cells were cultured in the presence of the inhibitors. These compounds were next examined for antiviral activity at later stages of the infection process. At a MOI of 0.01 infectious units/cell (GB8 virus), viral glycoproteins appear at the surface of JM cells by 24 hours post-infection (p.i.) and initiate fusion with neighboring CD4$^+$ cells; the syncytial numbers show a good correlation with the production of cell-free virus (Tyms et al., 1990). As is shown in Table 2, the addition of 100 µg/ml DIDS and H$_2$DIDS at 24 hours p.i. completely suppressed fusion relative to virus control when scored at 52 hours and 68 hours p.i. In fact, when DIDS was added as late as 43 hours p.i. to cultures containing substantial numbers of syncytial, these syncytia were completely absent by 68 hours p.i., and had significantly regressed in the H$_2$DIDS treated cultures. SITS, however, had no anti-syncytial activity relative to virus control although p24 antigen was slightly reduced, indicating a reduced antiviral effect. The relative order of antiviral potency of the stilbene disulfonic acids against established HIV-1 infections is consistent with that observed in acute infections, i.e., DIDS>H$_2$DIDS>>SITS suggesting a common mode of antiviral action at late and early stages of infection.

TABLE II

EFFECT OF DIDS, H$_2$DIDS AND SITS ON ESTABLISHED INFECTIONS OF HIV-1 (STRAIN GB8) IN JM CELLS

| Compound | Time of Addition (h)[a] | Syncytia[b] at time of addition | Synctia at 52 h[b] | Synctia at 68 h[b] | ng/ml P24 Antigen 75 h | |
|---|---|---|---|---|---|---|
| DIDS | 0 | 0 | 0 | 0 | Neg[c] | (0) |
| (100 µg/ml) | 24 | 0 | 0 | 0 | Neg | (0) |
| | 43 | 9 | 19 | 0 | 2.8 | (2.4%) |
| H$_2$DIDS | 0 | 0 | 0 | 0 | Neg | (0) |
| (100 µg/ml) | 24 | 0 | 0 | 0 | 2.4 | (2%) |
| | 43 | 9 | 19 | 3 | 16.4 | (14%) |
| SITS | 0 | 0 | 4 | 27 | 6.7 | (7.4%) |
| (100 µg/ml) | 24 | 0 | 35 | 77 | 21.7 | (18.6%) |
| | 43 | 9 | 59 | 80 | 49.3 | (42.3%) |
| Drug-free medium | 43 | 9 | 53 | 85 | 116.2 | (100%) |

[a]Time relates to hours p.i.
[b]Mean syncytia number (n = 3) at the time of addition of compound. During the period of incubation from 43 to 52 hours p.i. the mean number of syncytia increased from 9 to 53 synctia per well in the drug-free controls.
[c]Neg = no antigen detected.

Syncytial cell formation depends on the interaction of gp120, expressed in the membranes of infected cells, with the CD4 antigen on neighboring cells (Camerini and Seed, 1990). We utilized a cell cocultivation model to examine the effect of the stilbene disulfonic acids on the gp120-CD4 dependent fusion process. This system consists of mixing H9 cells chronically infected with HIV-1 RF (gp120$^+$ cells) with uninfected C8166 cells (CD4$^+$ cells) as the fusion indicator. In this assay, cell fusion occurred within 2 to 3 hours of mixing at 37° C. and substantial syncytia were observed after a further 3 to 4 hours (FIG. 1, Panel A). Treatment of cells with 100 µg/ml DIDS at the time of cell mixing completely prevented cell fusion (Panel B) while H$_2$DIDS only partially prevented syncytia (not shown). SITS at 200 µg/ml (Panel C) had no effect while DIDS at this concentration totally protected the C8166 cells for 5 days post-mixing (not shown). In parallel experiments, 10 µg/ml of 500,000 MW dextran sulfate (Panel E), like DIDS, completely inhibited relative to the nontreated virus control (Panel D); however, 250 µg/ml heparin (Panel F) and 100 µg/ml of 8,000 MW dextran sulfate (not shown) were totally ineffective. These findings with the sulfated polysaccharides were consistent with a previous report (Montefiori et al., 1990). Thus, where heparin and 8,000 MW dextran sulfate were ineffective at blocking virus-induced cell fusion and death, DIDS and H$_2$DIDS showed significant antiviral activity.

Figure 1A:
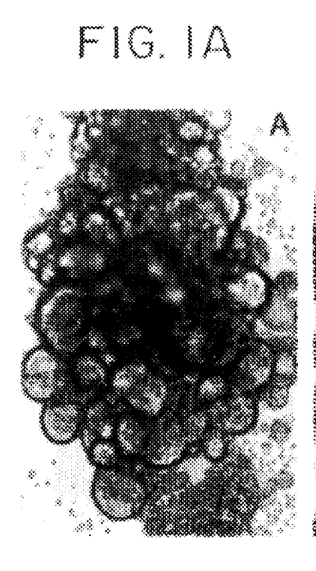
Figure 1B:
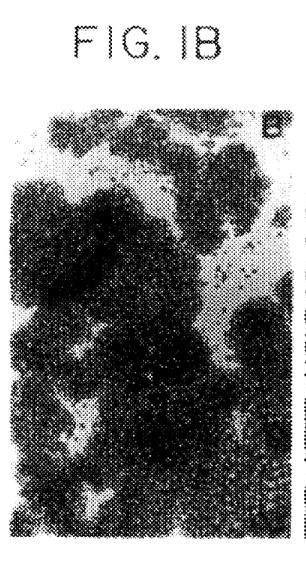
Figure 1C:
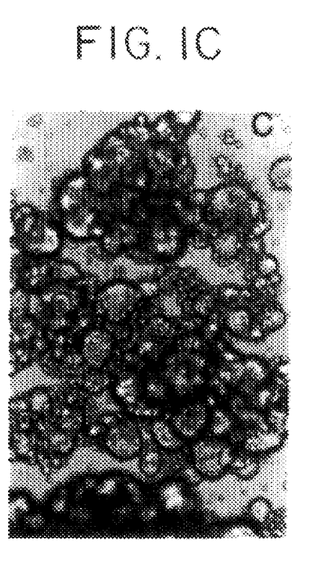
Figure 1D:
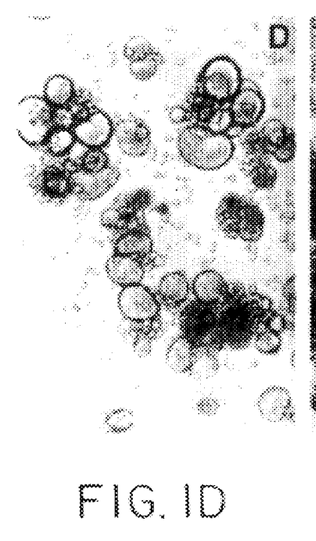
Figure 1E:
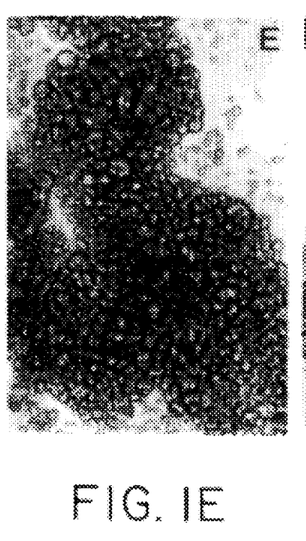
Figure 1F:
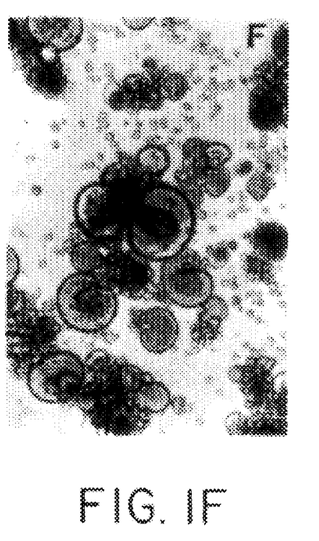
Figure 2A:
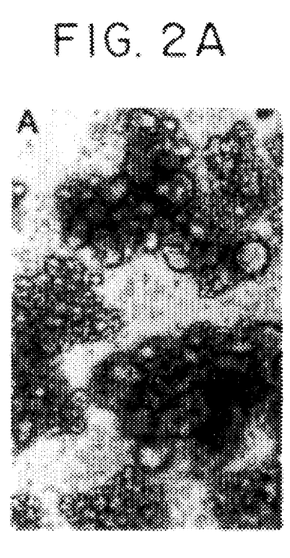
Figure 2B:
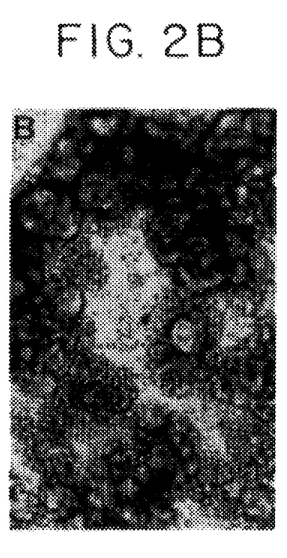
Figure 2C:
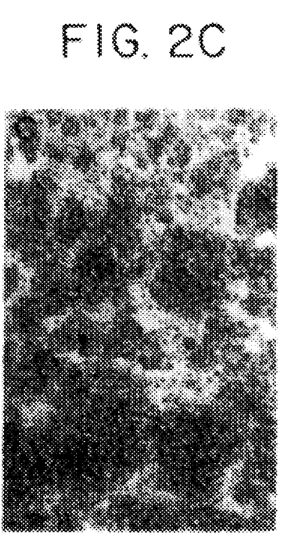

In the next experiments, CD4+ C8166 cells were pretreated overnight with either DIDS (100 µg/ml), SITS (100 µg/ml) or drug-free medium. Unabsorbed compounds were removed by repeated washings and chronically infected H9 cells were then added. As is shown in FIGS. 2A and B, pretreatment with SITS and drug-free medium, respectively, failed to block syncytia over the 6 hour observation period. In contrast, the DIDS-treated cells (FIG. 2C) remained syncytia-free. In contrast, no protective effect was observed when cells were pretreated with heparin or with 500,000

MW dextran sulfate. Thus, cell washing prior to mixing with the H9 cells oblated the protective effect observed above (FIG. 1, Panel E) when 500,000 MW dextran sulfate was continually present in the assay.

The amount of sulfated stilbene of formula 1 which is needed to prevent syncytium formation in HIV, HSV or CMV infected cells can be any effective amount. Experimentally, applicants have determined that sulfonated stilbenes when employed at a concentration of 50–100 µg/ml resulted in complete inhibition of syncytium formation as well as reduced the presence of P24 antigen, an indicator of HIV viral replication, to below $3.0 \times 10^2$. The amount of sulfonated stilbene of formula 1 to be administered in order to treat AIDS or ARC or other disease caused by HIV infection as well as diseases caused by HSV and CMV infection can vary widely according to the particular dosage unit employed, the period of treatment, the age and sex of the patient treated, the nature and extent of the disorder treated, and other factors well-known to those practicing the appropriate arts. Moreover sulfonated stilbenes of formula 1 can be used in conjunction with other agents known to be useful in the treatment of retroviral diseases and agents known to be useful to treat the symptoms of and complications associated with diseases and conditions caused by retroviruses. The anti-virally effective amount of sulfonic acid stilbenes of formula 1 to be administered will generally range from about 15 mg/kg to 500 mg/kg. A unit dosage may contain from 25 to 500 mg of the sulfonic acid stilbenes, and can be taken one or more times per day. The sulfonated stilbenes of formula 1 can be administered with a pharmaceutical carrier using conventional dosage unit forms either orally or parenterally.

For oral administration sulfonated stilbenes of formula 1 can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The sulfonated stilbenes of formula 1 may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly (ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the sulfonated stilbene in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

REFERENCE TO THE DRAWINGS

FIG. 1 The effect of the stilbene disulfonic acids and various sulfated polysaccharides on virus-induced cell fusion. In this assay, $10^5$ H9 cells, chronically infected with the HIV-1 strain RF, were cocultured with $10^5$ uninfected C8166 cells in the absence and presence of the test compounds. Panel A: Positive control, no compound addition; Panel B: 100 µg/ml DIDS; Panel C: 100 µg/ml SITS; Panel D: positive control; Panel E: 10 µg/ml 500,000 MW dextran sulfate; Panel F: 250 µg/ml heparin.

FIG. 2 Pretreatment of $CD4^+$ C8166 cells with DIDS blocks fusion with chronically infected H9 cells. In this experiment, C8166 cells were pretreated overnight with various stilbene disulfonic acids or drug-free medium (fusion control). The cells were washed, incubated with chronically infected H9 cells and syncytia were photographed at 6 hours post-mixing. Pretreatment conditions were as follows: Panel A: 100 µg/ml SITS; Panel B: drug-free medium; and Panel C: 100 µg/ml DIDS.

EXAMPLES

The following examples illustrate various aspects of this invention. The following information on reagents, cell lines, virus strains and assays apply to Examples 1–7.

EXPERIMENTAL PROCEDURES

Reagents 4,4'-diisothiocyanatostilbene-2,2'-disulfonic acid (DIDS), 4,4'-diisothiocyanatodihydrostilbene-2,2'-disulfonic acid ($H_2$DIDS) and 4-acetamido-4'-isothiocyanatostilbene-2,2'-disulfonic acid (SITS) were from Molecular Probes, Inc. (Eugene, Oreg.). These compounds were >95% pure by reverse-phase HPLC diode array analysis; the system employs a Hewlett Packard HP1040 detector coupled to a model 130A separation system (Applied Biosystems, Inc.) with an Aquapore RP-300 (2.1×30 mm) reverse-phase (C-8) column.

$CD4^+$ Cell Lines and HIV-1 Strains

The cell lines used were the semi-mature human lymphoblastoid leukemia T cell line JM, the human T-lymphoblastoid C8166 cell line, the human cutaneous T cell lymphoma line H9 and, the human T cell transformed line MT-4. Stocks of HIV-1 strains RF and GB8 (kindly provided by Dr. Graham Farrar, Center for Applied Microbiological Research, Porton Dawn, England) were prepared from chronically infected H9 cells and acutely infected JM cells, respectively. Virus stocks consisted of cell-free growth medium (RPMI 1640 plus 10% fetal calf serum) containing freshly shed virus. Virus titres were determined by a standard plaque reduction assay.

Virus Infection Assays

Virus stocks (strains RF or GB8) were diluted into growth medium containing various concentrations of DIDS, $H_2$DIDS or SITS. The required number of cells were then immediately added and the virus allowed to absorb for 2 hours at 37° C. to give a multiplicity of infection (MOI) of 0.001 infectious units/cell. The virus-infected cells were pelleted, washed three times in phosphate buffered saline (PBS), and resuspended in fresh growth medium containing the appropriate concentrations of stilbene disulfonic acids. Cells were then distributed into 24-well culture plates (Falcon) and assayed as described below for virus infection. Alternatively, cells were first infected with HIV-1 (strains RF or GB8) for 2 hours at 37° C. at the above MOI. After extensive washing, cells were replated into fresh growth medium containing various concentrations of stilbene disulfonic acids. In the above experiments, syncytia were scored between 2 and 4 days postinfection (p.i.) in triplicate using an Olympus CK2 inverted microscope. The culture fluids were recovered between 3 and 5 days p.i., clarified by low speed centrifugation (2,000 rpm) for 5 minutes and the level of HIV-1 p24 core antigen in the supernatants was determined by p24 antigen ELISA (Coulter). The concentrations of stilbene disulfonic acids giving 50% inhibition of HIV-1 growth ($IC_{50}$) were determined from the dose-response curves by linear regression analysis.

In post-treatment experiments, cells were first infected with HIV-1 strain RF or GB8 for 2 hours at 37° C. at a MOI of 0.01 and allowed to grow for either 24 or 43 hours before replating into fresh growth medium containing 100 µg/ml of DIDS, $H_2$DIDS or SITS. Syncytia were then scored at 52 and 68 hours p.i. in triplicate, and p24 viral core antigen in culture fluids were assayed at 75 hours p.i. as described above.

Anti-Syncytial Assay $CD4^+$ uninfected C8166 cells were seeded into 24-well trays (2×10$^5$ cells/well) that contained growth medium and various concentrations of test compounds. H9 cells, chronically infected with the RF strain of HIV-1, were washed and then added as a source of gp120$^+$ cells at 10$^5$ cells/well except for the noncytopathic control: those wells received uninfected H9 cells. The trays were then incubated at 37° C. and the cocultures were observed between 1 and 6 hours p.i. Syncytia were recorded on photographic film.

In pretreatment experiments, $CD4^+$ C8166 cells were maintained in serum-free medium (RPMI 1640 plus human transferrin 50 µg/ml, bovine insulin 20 µg/ml, bovine serum albumin 2 mg/ml) and were exposed to compound by overnight incubation. Treated cells were washed twice in fresh serum-free medium and then cocultured with chronically infected H9 cells in serum-free medium. Otherwise, cell numbers, assay conditions and scoring of syncytia were as described above.

Example 1

ANTIVIRAL ACTIVITY OF DIDS, $H_2$DIDS, AND SITS AGAINST HIV-1

Protocol: JM cells were infected with HIV-1 to give a multiplicity of infection of 0.001. Virus adsorption was for 2 hours at room temperature. The cells were washed and distributed into wells containing different concentrations of test compounds and incubated. After 2 days the cells were observed and syncytia were counted. The cell-free supernatant fluids were harvested at 4 and 6 days post infection and assayed for levels of p24 viral core antigen and after 6 days the supernatants were also titrated to determine levels of infectivity.

| Compound & Conc. | Mean Syncytial Counts 2 Days p.i. | p24 pg/ml 4 days p.i. | % Control | p24 pg/m. 6 days p.i. | % Control |
|---|---|---|---|---|---|
| Virus Control | 101 | $7.35 \times 10^4$ | 100% | $2.18 \times 10^6$ | 100% |
| SITS | | | | | |
| 100 µg/ml | 0 | $1.14 \times 10^3$ | 1.6% | $2.2 \times 10^4$ | 1% |
| 50 | 15 | $6.25 \times 10^4$ | 85% | $2.45 \times 10^5$ | 11.2% |
| 25 | 63 | $1.53 \times 10^5$ | 100% | $1.26 \times 10^6$ | 58% |
| 12.5 | 63 | $1.85 \times 10^5$ | 100% | $1.51 \times 10^6$ | 69% |
| 6 | 72 | — | — | — | — |
| 3 | 93 | — | — | — | — |
| DIDS | | | | | |
| 100 µg/ml | 0 | None detected | 0 | $4.87 \times 10^2$ | 0.02% |
| 50 | 0 | $1.3 \times 10^2$ | 0.18% | $1.23 \times 10^4$ | 0.56% |
| 25 | 0 | $4.7 \times 10^3$ | 6.4% | $1.21 \times 10^6$ | 56% |
| 12.5 | 31 | $1.1 \times 10^5$ | >100% | $2.44 \times 10^6$ | >100% |
| 6 | 101 | — | — | — | — |
| 3 | 114 | — | — | — | — |
| $H_2$DIDS | | | | | |
| 100 µg/ml | 0 | None detected | 0 | $6.48 \times 10^2$ | 0.03% |
| 50 | 0 | $7.0 \times 10^1$ | 0.01% | $3.77 \times 10^2$ | 0.02% |
| 25 | 7 | $3.2 \times 10^4$ | 43% | $2.66 \times 10^6$ | >100% |
| 12.5 | 71 | $9.4 \times 10^4$ | >100% | $8.51 \times 10^6$ | >100% |
| 6 | 97 | — | — | — | — |
| 3 | 107 | — | — | — | — |

| BACK TITRATION OF CELL-FREE SUPERNATANTS AT 6 DAYS p.i. (SFUs)* | | |
|---|---|---|
| COMPOUND | µg/ml | *SFUs/ml |
| DIDS | 100 | <10¹/ml |
|  | 50 | <10¹/ml |
|  | 25 | Not done |
|  | 12.5 | 2.4 × 10³/ml |
| SITS | 100 | <10¹/ml |
|  | 50 | <10¹/ml |
|  | 25 | 1.9 × 10³/ml |
|  | 12.5 | 2.1 × 10³/ml |
| SITS | 100 | <10¹/ml |
|  | 50 | 4.8 × 10³ |
|  | 25 | 2.5 × 10³ |
|  | 12.5 | 4.9 × 10³ |
| Virus Control | — | 2.6 × 10³ |

*Syncytia-forming unit; cell-free supernatants from virus infected cells having received the indicated concentration of compounds were incubated with fresh uninfected JM cells and syncytia were scored to determine the number of infectious units/ml. These results were compared to the cell-free supernatants from virus-infected control cells not having received drug treatment.

Example 2

TREATMENT OF HIV-1 INFECTED CELLS WITH DIDS, SITS, AND ddC

Protocol: JM cells were infected with HIV to give approximately 100 syncytia after 3 days. Virus adsorption was at room temperature for 2 hours. The cells were then washed thoroughly and distributed in wells of a tissue culture plate at a concentration of $1\times10^5$ cells/well. At 24 hours post infection either DIDS (100 µg/ml), SITS (100 µg/ml), or ddC (5 µM) were added to wells having infected cells. As virus controls, some wells had no drug added. At 42 hours post infection other wells received either ddC (5 µM), SITS (100 µg/ml), or DIDS (100, 50, 25, 12.5, 6.25 µg/ml). Syncytia were scored at 3 and 4 days post-infection and the supernatant fluids were harvested after 3 and 4 days for p24 core antigen determination.

Results:

| COMPOUND and Time of Addition | CONC. | MEAN SYNCYTIA /WELL 3 DAYS p.i. | p24 ANTIGEN pg/ml 3 DAYS p.i. | % CONTROL |
|---|---|---|---|---|
| Virus Control | — | >100 | 4.7 × 10⁴ | 100 |
| DIDS at 24 hr | 100 µg/ml | 0 | 6.1 × 10³ | 13 |
| DIDS at 42 hr | 100 µg/ml | 34 | 1.98 × 10⁴ | 42 |
|  | 50 µg/ml | >80 | 1.92 × 10⁴ | 41 |
|  | 25 µg/ml | As VC | 1.50 × 10⁴ | 32 |
|  | 12 µg/ml | As VC | 2.10 × 10⁵ | >100 |
|  | 6 µg/ml | As VC | 1.80 × 10⁴ | 38 |
| SITS 24 hr | 100 µg/ml | 1.80 × 10⁴ |  | 38 |
| SITS 42 hr | 100 µg/ml | As VC | 7.00 × 10³ | 15 |
| ddC 24 hr | 5 µM | 65 | 9.00 × 10³ | 19 |
| ddC 42 hr | 5 µM | As VC | 1.70 × 10⁴ | 36 |

| COMPOUND | CONC. | MEAN SYNCYTIA /WELL 4 DAYS p.i. | p24 ANTIGEN pg/ml 4 DAYS p.i. | % CONTROL |
|---|---|---|---|---|
| Virus Control | — | >150 | 8.95 × 10⁴ | 100 |
| DIDS 24 hr | 100 µg/ml | 20 | 1.58 × 10⁴ | 18 |
| DIDS 42 hr | 100 µg/ml | 70 | 2.09 × 10⁴ | 23 |
|  | 50 µg/ml | 100 | 6.3 × 10⁴ | 70 |
|  | 25 µg/ml | As VC | 5.9 × 10⁴ | 66 |
|  | 12 µg/ml | As VC | 3.9 × 10⁵ | 44 |
|  | 6 µg/ml | As VC | 3.4 × 10⁴ | 38 |
| SITS 24 hr | 100 µg/ml | As VC | 6.25 × 10⁴ | 70 |
| SITS | 100 µg/ml | As VC | 9.5 × 10⁴ | >100 |
| ddC 24 hr | 5 µM | 51 | 3.1 × 10³ | 3.5 |
| ddC 42 hr | 5 µM | As VC | 6.7 × 10⁴ | 75 |

Example 3

ANTI-HIV ACTIVITY OF DIDS, SITS, H₂DIDS

Protocol: H9 cells chronically infected with RF strain of HIV-1 and uninfected C8166 cells were mixed in the presence of either DIDS, SITS, H₂DIDS, dextran sulfate, or heparin (100 µg/ml). the cells were observed after 2, 3½ and 5½ hours and the amount of cell fusion quantified.

Results:

| COMPOUND | CONC. | Syncytia after 2 hrs | after 3 ½ hrs | after 5 ½ hrs |
|---|---|---|---|---|
| Virus Control | — | ++ | +++ | +++ |
| DIDS | 100 µg/ml | 0 | 0 | 0 |
| SITS | 100 µg/ml | ++ | ++ | ++ |
| H₂DIDS | 100 µg/ml | 0 | 0 | 0 |
| Heparin | 100 µg/ml | ++ | +++ | +++ |
| Dextran Sulfate | 100 µg/ml | 0/+ | 0 | 0 |

Example 4

INHIBITION OF HIV INDUCED CELL FUSION AFTER PRETREATMENT OF UNINFECTED CELLS WITH DIDS, SITS AND H₂DIDS

Protocol: C8166 cells were pretreated for 2.5 hours with either DIDS, SITS or H₂DIDS (at 500 and 250 µg/ml). The cells were then washed three times and mixed with H9 cells chronically infected with HIV-1. Cell fusion was quantified after 4 and 24 hours.

Results:

| COMPOUND | CONC. | Syncytial Scores 4 hrs p.i. | 24 hrs p.i. |
|---|---|---|---|
| Virus Control | — | ++++ | ++++ |
| SITS | 500 µg/ml | +++/++++ | ++++ |
|  | 250 µg/ml | +++/++++ | ++++ |
| DIDS | 500 µg/ml | + | +++ |
|  | 250 µg/ml | ++/+++ | +++ |
| H₂DIDS | 500 µg/ml | + | +++ |
|  | 250 µg/ml | ++/+++ | ++++ |

Example 5

ANTI-HIV ACTIVITY OF DIDS, SITS AND H₂DIDS

Protocol: H9 cells chronically infected with HIV-1 and uninfected C8166 cells were mixed in the presence of either DIDS, SITS, H₂DIDS, dextran sulfate, heparin (at 100 μg/ml), OKT4 or OKT4A (at a 1/50 dilution). The cells were observed after 4 hours and the amount of cell fusion quantitied. OKT4 and OKT4A are monoclonal antibodies that bined the CD4 cell surface antigen.
Results:

| COMPOUND | CONC. | Syncytia after 4 hrs |
|---|---|---|
| Virus Control | — | +++ |
| DIDS | 100 μg/ml | 0/+ |
| H2DIDS | 100 μg/ml | 0/+ |
| SITS | 100 μg/ml | +++ |
| Heparin | 100 μg/ml | +++ |
| Dextran sulfate (8,000) | 100 μg/ml | ++ |
| Dextran sulfate (500,000) | 100 μg/ml | 0 |
| OKT4 | 1/50 | +++ |
| OKT4A | 1/50 | 0 |

Example 6

EFFECTS OF DIDS, H₂DIDS AND SITS ON ESTABLISHED INFECTIONS OF HIV-1

Protocol: JM cells were infected with HIV at a multiplicity of infection of 0.00025 syncytial forming units per cell. Virus adsorption was at room temperature for one hour. The cells were then washed three times and distributed in wells of a tissue culture plate at a concentration of $2 \times 10^5$ cells/well. Either DIDS, SITS or H₂DIDS (all at 100 μg/ml) were added to wells at 0, 24, 43 and 51 hours post-infection. As virus controls some wells had no drug added. Syncytia were scored at 43, 52 and 68 hours post-infection. the cell-free supernatant fluids of the virus control wells were harvested after 33, 43, 51, 68 and 75 hours post-infection. All other wells were harvested 75 hours post-infection. The supernatant fluid was then assayed for p24 viral core antigen.
Results:

Time course of syncytial formation and p24 Antigen Production

| Time | Mean Syncytia | P24 pg/ml |
|---|---|---|
| 33 hours | 0 | neg (<10³) |
| 43 hours | 9 | neg |
| 51 hours | 53 | 2383 |
| 68 hours | 85 | 13678 |
| 75 hours | 0 | 116196 |

P24 Antigen (75 hours post-infection) (pg/ml)

| Compound | Time of Addition (hours) | | | |
|---|---|---|---|---|
| | 0 | 24 | 43 | 51 |
| DIDS 100 μg/ml | Neg >1% | Neg <1% | 2793 2.4% | 49050 42% |
| SITS | 8680 | 21669 | 49245 | 53830 |
| 100 μg/ml | 7.4% | 18.6% | 42.3% | 47.2% |
| H₂DIDS 100 μg/ml | Neg <1% | 2363 2% | 16412 14% | 42020 36% |

Syncytial Scores

| COMPOUND | Time of Addition (hours) | | Mean Syncytia 51 hrs | Mean Syncytia 68 hrs |
|---|---|---|---|---|
| DIDS | 0 h | (0)* | 0 | 0 |
| | 24 h | (0) | 0 | 0 |
| | 43 h | (9) | 19 | 0 |
| | 51 h | (53) | — | 25 |
| SITS | 0 h | (0) | 4 | 27 |
| | 24 h | (0) | 35 | 77 |
| | 43 h | (9) | 59 | As VC |
| | 51 h | (53) | — | As VC |
| H₂DIDS | 0 h | (0) | 0 | 0 |
| | 24 h | (0) | 0 | 0 |
| | 43 h | (9) | 19 | 3 |
| | 51 h | (53) | — | 15 |
| Virus Control | — | | 53 | 85 |

*Mean Syncytia at time of addition of compound

Example 7

EFFECT OF SULFONATED STILBENES ON HSV AND CMV GROWTH

Protocol: Plaque reduction assay. Treatment after adsorption during incubation.
Results—HCMV:

| COMPOUND | CONC. μg/ml | PLAQUE COUNTS | | | | MEAN % VC |
|---|---|---|---|---|---|---|
| DIDS | 1000 μg | 0 | 0 | 0 | | 0 |
| | 100 | 3 | 4 | 3 | | 10% |
| | 10 | 16 | 12 | 11 | | 43% |
| | 1 | 15 | 14 | — | | 49% |
| Virus Control | — | 34 | 30 | 31 | 27 | 100% |

| COMPOUND | CONC. | COUNTS | | | | MEAN % VC |
|---|---|---|---|---|---|---|
| HCMV | | | | | | |
| Gancyclovir | 1000 μg/ml | 0 | 0 | 0 | | 0 |
| | 10 | 3 | 2 | 7 | | 10% |
| | 1 | 6 | 13 | 1 | | 22% |
| | 0.1 | 34 | 39 | — | | >100% |
| Virus Control | — | 30 | 31 | 27 | 34 | 100% |
| HSV 2 | | | | | | |
| DIDS | 100 μg/ml | 0 | 0 | 0 | | 0 |
| | 10 | 25 | 25 | 25 | | 44% |
| | 1 | 31 | 33 | 39 | | 61% |
| | 0.1 | 37 | 40 | — | | 68% |
| Virus Control | — | 65 | 51 | 58 | 51 | 100% |
| H₂DIDS | 100 μg/ml | 0 | 0 | 0 | | 0 |
| | 10 | 26 | 19 | 21 | | 43% |
| | 1 | 23 | 31 | 24 | | 46% |
| | 0.1 | 35 | 35 | — | | 63% |
| Virus Control | — | 27 | 20 | 24 | 25 | 100% |
| HSV2 | | | | | | |
| SITS | 100 μg/ml | 16 | 13 | — | | 63% |
| | 10 | 25 | 25 | 24 | | 100% |
| | 1 | 28 | 25 | 23 | | 100% |
| | 0.1 | 34 | 26 | — | | >100% |

-continued

| Virus Control | — | 27 | 20 | 24 | 25 | 100% |
|---|---|---|---|---|---|---|
| Acyclovir | 100 µg/ml | 0 | 0 | 0 | | 0 |
| | 10 | 0 | 1 | 0 | | 0 |
| | 1 | 31 | 31 | 29 | | 54% |
| | 0.1 | 44 | 34 | — | | 70% |
| Virus Control | — | 65 | 51 | 58 | 51 | 100% |

What is claimed is:

1. A method of treating a viral infection selected from HSV and CMV, in a patient in need thereof comprising administering to the patient an antivirally effective amount of a compound of the formula wherein $R_1$ and $R_2$ are each independently a S=C=N— or $CH_3C(O)NH$— group, B is a —$CH_2$—$CH_2$— group, and $M_1$ and $M_2$ are each independently a hydrogen or pharmaceutically acceptable cation.

2. A method of claim 1 wherein the sulfonyl groups are at the ortho position.

3. A method of claim 1 wherein $M_1$ and $M_2$ are each independently a hydrogen or a sodium cation.

4. A method of claim 1 wherein the compound is 4,4'-diisothiocyanatodihydrostilbene-2,2'-disulfonic acid.

* * * * *